United States Patent [19]

Suzuki et al.

[11] 4,415,559

[45] Nov. 15, 1983

[54] ANTICOAGULANT

[75] Inventors: Suguru Suzuki, Tokyo; Noritoshi Sano, Kawasaki; Tetsuya Tajima, Nagareyama, all of Japan

[73] Assignee: Eisai Co., Ltd., Tokyo, Japan

[21] Appl. No.: 345,834

[22] Filed: Feb. 4, 1982

[30] Foreign Application Priority Data

Feb. 12, 1981 [JP] Japan ................................ 56-17994

[51] Int. Cl.³ .......................................... A61K 31/725
[52] U.S. Cl. .................................................. 424/183
[58] Field of Search ......................................... 424/183

[56] References Cited

U.S. PATENT DOCUMENTS 4,119,774 10/1978 Andersson et al. ................... 536/21

OTHER PUBLICATIONS

Lam, L. et al., Biochem. Biophys. Res. Comm., 69(2), 570–577 (1976).

*Primary Examiner*—Richard A. Schwartz
*Attorney, Agent, or Firm*—Flynn, Thiel, Boutell & Tanis

[57] ABSTRACT

An anticoagulant containing heparin having low antithrombin III affinity as an effective ingredient.

8 Claims, 1 Drawing Figure

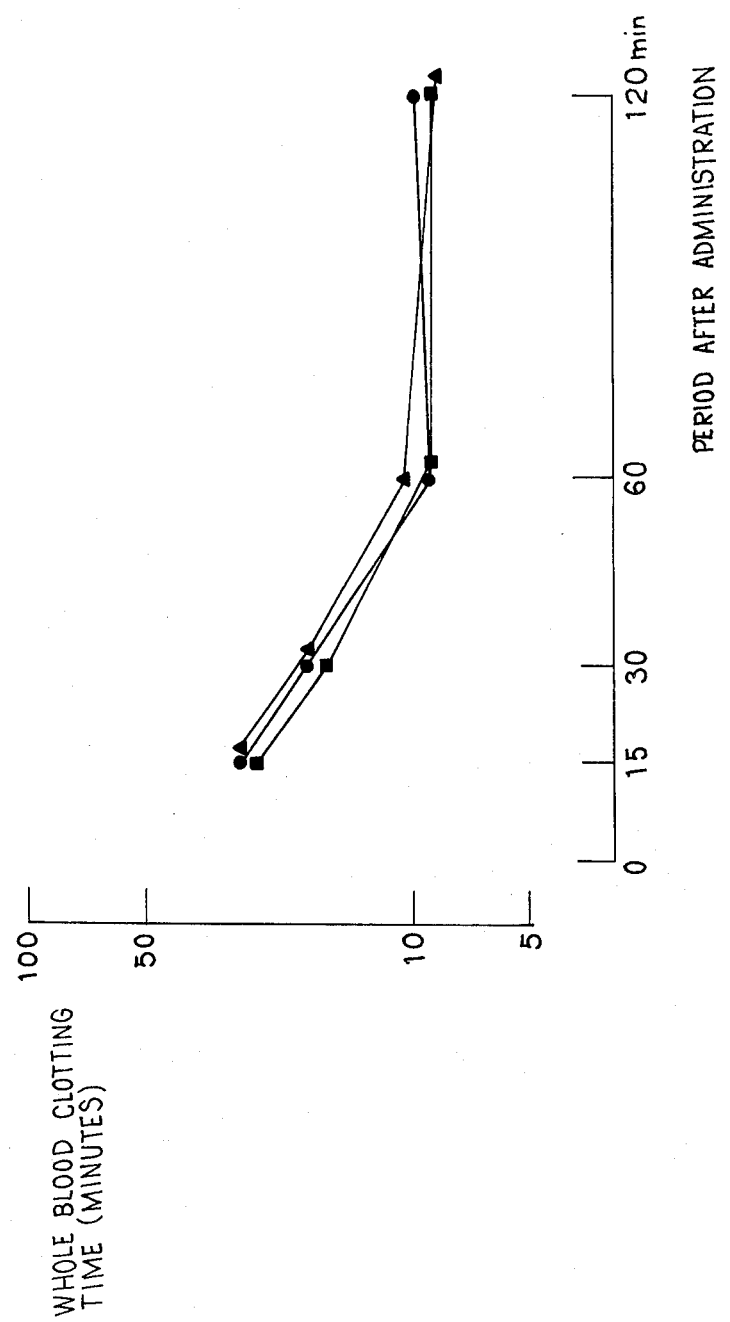

ANTICOAGULANT

This invention relates to an anticoagulant containing heparin having low antithrombin III affinity as an effective ingredient and which provides a reduced danger of hemorrhage.

It is known that blood coagulation can be classified into an exogenous coagulation mechanism in which coagulation occurs due to the participation of tissue thromboplastin and an endogenous coagulation mechanism in which coagulation occurs due solely to the coagulating factors in the blood as the Factor XII in the blood is activated.

The exogenous coagulation mechanism is characterized in that substances not present in the blood, or the tissue factor (tissue thromboplastin), activate the Factor VII in the blood, the Factor VII thus activated (Factor VIIa) forms a complex together with the tissue thromboplastin and the resulting complex in turn activates the Factor X.

The endogenous coagulation mechanism is characterized in that the Factor XII (the Hageman factor) is activated due to the surface contact of a substance, the Factor XII thus activated (Factor XIIa) activates the Factor XI, the Factor XI thus activated (Factor XIa) in turn activates the Factor IX and the activated Factor IX (Factor IXa) activates the Factor X in cooperation with the Factor VIII and the like.

Incidentally, the process from the activation of prothrombin by the activated Factor X (Factor Xa) in cooperation with the Factor V and the like until the final stage of blood coagulation is common to both mechanisms.

Recently, antithrombin III (AT III) has drawn increasing attention in conjunction with diseases relating to blood coagulation. This is because antithrombin III is capable of inhibiting almost all of the blood coagulating factors and plays an important role in the controlling mechanism of the blood coagulation reaction.

Antithrombin III is a glycoprotein belonging to $\alpha_2$-macroglobulin, and it consists of a single-stranded polypeptide bonded with about 10% sugar and has three intramolecular disulfide bonds. The amino acid composition is characterized by having a high basic amino acid content, especially a high lysine content. Antithrombin III is capable of inhibiting almost all of the active blood coagulating factors and, according to the immunological data, antithrombin III is said to effect 75% of the thrombin-inhibiting activity. Its clinical importance is also obvious from the fact that phlebothromboembolism frequently occurs in patients having antithrombin III deficiency. The concentration of antithrombin III in blood, in a condition of antithrombin III deficiency, drops to at most 40–50% of the normal concentration. This suggests that antithrombin III plays a vital role in the equilibrium in the blood coagulation system and when its concentration in blood is below 40–50% of the normal concentration, the condition can be fatal.

It is believed that the inhibiting action of antithrombin III in the blood plasma occurs as the alginine moiety in the molecule combines with the active serine moiety of various serine protease groups forming the blood coagulation system, thereby to form a stable complex and thus to inhibit their enzymatic activity. The rate of the formation reaction of this complex is rather slow, but if heparin is present in the reaction system, heparin combines with antithrombin III in a specific manner and changes its steric structure, accelerating the rate of the bonding between antithrombin III and the serine protease groups by 300 to 500 times. This reaction-promoting activity of heparin is a peculiar phenomenon that can be observed only with antithrombin III, but not with the other inhibiting factors. In other words, heparin provides an important effect on the blood coagulation system via antithrombin III.

This effect of heparin can scarcely be observed in other acidic mucopolysaccharides, other than heparin. This fact suggests that the antithrombin III activity-promoting effect of heparin is closely related with the number and kind of the sulfuric acid groups present in heparin, and means that in the so-called "heparin therapy", the purity of the heparin or the fractionation and purification of heparin remains as a very important problem yet to be solved. In other words, when heparin is fractionated by a suitable method, it is still necessary to clarify the relationship between each fraction and antithrombin III and the direct relationship between each fraction and the blood coagulation system itself.

It has been believed, to this date, that one of the important aspects in heparin therapy is how to make heparin exhibit its function as the reaction catalyst for the coagulation inhibiting reaction caused by antithrombin III. However, the present state of the art of heparin therapy involves the following fundamental drawbacks and no suitable solution has yet been provided for them.

First, as described above, heparin catalyzes the inhibiting reaction caused by antithrombin III but heparin is not free from the problem that it directly combines with antithrombin III and lowers the concentration of free antithrombin III in the blood, thereby causing the so-called hypoantithrombinemia condition. Commercially available heparin, that has been used conventionally, has high antithrombin III affinity and causes hypoantithrombinemia. As a result, it enhances the tendency to bleed as a side effect.

Second, there is a large variability in the purity of heparin now in use. Heparin, as a product, is extremely non-uniform. Commercially available heparin is produced using intestinal membranes of pigs, sheep and cows and the lungs and intestinal membranes of whales as the industrial starting materials. When its activity is measured in accordance with the standards of the British or Japanese Pharmacopeia, the activity varies from product to product. Moreover, a number of reports are filed to the effect that the results of such measurements do not always reflect the activity of heparin in vivo.

Under these circumstances, it can be fairly said that studies on the improvement of heparin therapy are primarily directed to the preparation of high-purity, high-unit (high Japanese Pharmacopeia Heparin Units) heparin, whereby to minimize the clinical dose of heparin required and eventually to reduce the problems, such as hypoantithrombinemia and the like as much as possible.

Thus, Rosenberg et al found that a heparin fraction having a high affinity for human antithrombin III (called "High Affinity Heparin") and a heparin fraction having a low affinity for human antithrombin III (Called "Low Affinity Heparin") exist in heparin in a stoichiometric ratio of about 1:2. They reported that anticoagulation activity is scarcely observed with Low Affinity Heparin, but High Affinity Heparin exhibits two to three times as high an anticoagulation activity as that of the non-fractionated heparin. This suggests a direction of improvement in that High Affinity Heparin is a very high-purity and high-unit heparin that would make it possible to reduce the clinical dose and would restrict the decrease of antithrombin III and hence would provide an extremely advantageous clinical effect. U.S. Pat. No. 4,119,774 can be mentioned as prior art relating with this finding. This prior art discloses the technique of purifying heparin using an adsorbent (lattice-bound antithrombin bonded with plasma protein) and increasing its specific activity, on the assumption that any bad side effect caused by heparin results from impurities contained in the heparin preparation.

The inventor of the present invention has carried out studies on heparin therapy on the basis of the prior art described above and has discovered the following novel fact.

Namely, the inventor of the present invention has obtained a substance, namely, heparin having low antithrombin III affinity, which will be defined later and corresponds to the "Low Affinity Heparin" of Rosenberg et al, *Biochemical and Biophysical Research Communications,* Vol. 69, No. 2, pp. 570–577 (1976).

It was found that this substance is one that hardly exhibits any inhibiting activity against the exogenous coagulation, but it exhibits activity more specifically against the endogenous coagulation as will be illustrated later in Examples 1 through 3, in addition to its low affinity for antithrombin III.

The characteristic properties of this substance can be summarized as follows. (1) It has low antithrombin III affinity. (2) It has scarcely any inhibiting activity against exogenous coagulation. (3) It exhibits significant inhibiting activity more specifically against endogenous coagulation.

Commercially available heparin used heretofore has a tendency to cause bleeding and thus causes thrombosis due to the decrease of antithrombin III in long-term heparin therapy. However, it is expected that heparin having low antithrombin III affinity, in accordance with the present invention, will be a drug that does not cause thrombosis due to the decrease of antithrombin III, even in long-term therapy, it has less tendency to cause bleeding and it exhibits a sufficiently high anticoagulation activity. In fact, as will be shown in Example 4, the composition of the present invention is a safe anticoagulant having a reduced tendency to cause bleeding.

Among the characteristic properties described above, the fact (3) was discovered by the inventor of the present invention and the present invention has been perfected on the basis of this discovery.

The present invention will now be described in further detail in connection with the Examples given below. [a] The measuring method of heparin activity stipulated in the Pharmacopeia in many countries of the world is primarily directed to measuring the inhibiting activity in exogenous coagulation.

For instance, the item of the determination method of "heparin sodium" in the Japanese Pharmacopeia, 9th Edition, sets forth a method of measuring the clotting time by mixing heparin, thrombokinase extract and blood. In short, this determines the heparin activity by means of its inhibiting activity in exogenous coagulation. (Refer to "Heparin", supervised by Zensaku Yoshizawa, published by Kodansha, page 134).

As will be illustrated in the Experimental Example 1, when the heparin activity was measured for the heparin having low antithrombin III affinity, according to the present invention, in accordance with the method as set forth in the Japanese Pharmacopeia, the activity was found to be almost nil. It was thus found that the heparin having low antithrombin III affinity, according to the invention, had scarcely any inhibiting activity against exogenous coagulation, and the aforementioned feature (2) was confirmed. [b] Next, the existence of the inhibiting activity against endogenous coagulation will be evidenced if a prolongation of time is observed in the whole blood clotting time when such a clotting time is measured by preparing first a system which causes coagulation solely by contact factors with no application at all of exogenous coagulating factors, that is, an endogenous coagulation system, and then adding heparin to the system. In other words, since it has been known that heparin inhibits each of the Factors XIIa, XIa, IXa and Xa and thrombin in cooperation with antithrombin III in the blood plasma, if any prolongation is observed upon measurement of the whole blood clotting time of the system, to which application of the exogenous coagulating factors is prevented and to which heparin is added, as will be illustrated in Experimental Example 2, the delay is attributable to inhibition by heparin of endogenous coagulation. More definitely, the results obtained in Experimental Example 2 are as follows. When compared with heparin having high antithrombin III affinity (which will be defined later in conjunction with the present invention) or with heparin calcium (a heparin drug readily available commercially under the trademark "Hepacalin"), the necessary dose of the heparin having low antithrombin III affinity, in accordance with the present invention, is found to contain 1/5 in unit of the former, wherein the comparison is made in terms of the quantity or potency required for doubling the ordinary whole blood clotting time. In other words, heparin having low antithrombin III affinity, in accordance with the present invention, exhibits a specific inhibiting action against endogenous coagulation and the magnitude of its activity is found to be five times greater that of the above-mentioned heparin having high antithrombin III affinity or heparin calcium. Thus, the aforementioned feature (3) is confirmed. [c] The inventor of this invention has further examined the duration of the inhibiting activity against endogenous coagulation, because heparin would fail to exhibit a satisfactory effect as an anticoagulant if its inhibiting activity did not last, however high its initial activity may be. As will be illustrated in Example 3, therefore, (1) heparin having low antithrombin III affinity, (2) heparin having high antithrombin III affinity and (3) heparin calcium, were compared with one another as to their efficacy after a predetermined period of time (the whole blood clotting time) while their inhibiting activity against endogeneous coagulation was maintained at the same level, that is to say, by dosing the low affinity heparin (1) in an amount providing 1/5 of the Heparin Units provided by the dosages of high affinity heparin (2) and heparin calcium (3). The results were found to be the same. It is thus established that the three heparins (1), (2) and (3) have the same duration of anticoagulating action against endogenous coagulation. [d] The greatest side effect of heparin is that it causes bleeding and prolongs the bleeding time. It is well known that the strength of the inhibiting activity against exogenous coagulation is closely correlated with the danger of bleeding. As described above, however, heparin having low antithrombin III affinity, in accordance with the present invention, exhibits a more selective inhibiting activity against endogenous coagulation compared with heparin having high antithrombin III affinity and heparin calcium and the dose of the low affinity heparin of the present invention can be 1/5 of the dosages of the other two heparin materials. This fact suggests that heparin having low antithrombin III affinity will be a safe anticoagulant having reduced danger of bleeding.

In order to evidence the above, the inventor of this invention has compared the bleeding time after administration, as will be illustrated in Example 4, and found that heparin having low antithrombin III affinity, in accordance with the present invention, provides a shorter prolongation of bleeding time and therefore exhibits a lesser danger of bleeding than the other two heparin materials. [e] When the acute toxicity of heparin having low antithrombin III affinity, according to the present invention, was tested, the $LD_{50}$ in intravenous administration was found to be at least 1000 mg/kg.

The "heparin having low antithrombin III affinity", according to the present invention is one having low antithrombin III affinity at a physiological pH and in a physiological salt concentration corresponding to those of a living human body. As a definite substance, it can be stipulated by the following definite method for its preparation.

First, antithrombin III is bonded to a lattice, such as cephalose, to form a lattice-bound antithrombin III and an affinity-chromatography column is prepared therefrom. Affinity chromatography is then carried out at a physiological pH and in a physiological salt concentration by applying commercially available heparin that has been conventionally employed in therapeutics, such as said heparin calcium.

Heparin that is not adsorbed by a lattice-bound antithrombin III, but rather is eluted during this chromatography procedure, is "heparin having low antithrombin III affinity" in accordance with the present invention.

The term "lattice" used herein refers to cephalose 4B or the like, but the present invention is not limited thereto.

The term "lattice-bound antithrombin III" denotes such antithrombin III that is obtained by bonding antithrombin III extracted in advance from the blood plasma to the lattice, and it can be prepared in the following manner.

200 mg of antithrombin III is dissolved in 200 ml of 0.2M $NaHCO_3$ (pH 9.0) and the solution is added to cephalose CL-4B gel activated by cyanogen bromide for suspension and is gently stirred at 4° C. for 24 hours. The solution is filtered and is washed several times with 0.2M $NaHCO_3$ (pH 9.0). Finally, it is suspended in 0.2M $NaHCO_3$ (pH 9.0).

The term "physiological pH" represents the range of pH of 7 to 8 and the term "physiological salt concentration" means a concentration in the range of 0.05M to 0.20M, calculated as the sodium chloride concentration. Accordingly, the predetermined condition can be satisfied by making use of a 0.05M tris-hydrochloric acid buffer (pH 7.5, 0.05M~0.20M NaCl), for example. However, the present invention is not limited to the tris-hydrochloric acid buffer and any buffer can be used so long as it satisfies the physiological pH and physiological salt concentration stipulated hereby.

The term "heparin having high antithrombin III affinity" refers to one having the opposite concept to the "heparin having low antithrombin III affinity", in accordance with the present invention. The term represents heparin having high antithrombin III affinity at the physiological pH and physiological salt concentration of the living body. As one definite preparation method, the heparin adsorbed by the lattice-bound antithrombin III, at the physiological pH and physiological salt concentration, can be defined as heparin having high antithrombin III affinity. This heparin having high antithrombin III affinity can be isolated from the heparin having low antithrombin III affinity by once allowing it to be adsorbed by the lattice-bound antithrombin III at the physiological pH and physiological salt concentration, then keeping only the pH at the physiological pH, and carrying out affinity chromatography by increasing the salt concentration to exceed the physiological concentration, thereby desorbing the heparin having high antithrombin III affinity from the lattice-bound antithrombin.

The anticoagulant of the present invention is formulated as an injectable solution and the drug is administered either intravenously intramuscularly of subcutaneously. The injectable solution typically comprises the anticoagulant of the present invention and water or isotonic saline. The suitable dose per day is from 10 to 5000 units (Japanese Pharmacopeia Heparin Units) to a human being, but this dosage range is illustrative, not limitative.

BRIEF DESCRIPTION OF THE DRAWING

The drawing is a graph illustrating the results described in item "5. Results" in Experimental Example 3. It is a diagram showing the change in the whole blood clotting time (average of four cases) at a predetermined period after administration of heparin materials. In the drawing, the symbols assigned to the lines represent the changes in the clotting time in the case where 100 μ/kg of heparin having high antithrombin III affinity as defined in the present specification was intravenously administered (symbol ■ ), the case where 20 μ/kg of heparin having low antithrombin III affinity in accordance with the present invention was intravenously administered (symbol ● ) and the case where 100 μ/kg of heparin calcium was intravenously administered (symbol ▲ ), respectively.

The following Experimental Examples will further describe and clarify the effect of the present invention.

EXPERIMENTAL EXAMPLE 1

1. Samples
   heparin calcium
   heparin having high antithrombin III affinity as defined in this specification
   heparin having low antithrombin III affinity, in accordance with this invention
2. Animals used
   White male native rabbits weighing from 3.0 to 3.6 kg were kept for at least one month in a chamber at 21° to 24° C. They were fed 100 g of a solid feed for rabbits, "ORC-4" (produced by Oriental Kobo K.K.) every day and were permitted to take service water freely.
3. Method of experiment
   Heparin Unit (μ)
   The Heparin Unit was determined in terms of the exogenous coagulation inhibiting activity in accordance with the Japanese Pharmacopeia, sometimes hereinafter referred to as JP.

(a) Preparation of standard solutions

A heparin solution of a known Heparin Unit concentration was diluted with a 5% glucose solution to prepare 8.53 μ/ml (high concentration standard solution, sometimes referred to as "SH" hereinafter) and 6.83 μ/ml (low concentration standard solution, sometimes referred to as "SL" hereinafter), respectively.

(b) Preparation of sample solutions 10.1 mg of heparin calcium, 6.6 mg of heparin having high antithrombin III affinity as defined in the present specification and 9.5 mg of heparin having low antithrombin III affinity, in accordance with the present invention, were accurately measured and were dissolved in 200 ml, 400 ml, and 20 ml of a 5% glucose solution, respectively, to prepare high-concentration sample solutions $T_1H$, $T_2H$ and $T_3H$ (sometimes collectively referred to as "TH" hereinafter). 8 ml of each of these high-concentration sample solutions was diluted to 10 ml by a 5% glucose solution, thereby forming low-concentration sample solutions $T_1L$, $T_2L$ and $T_3L$ (sometimes collectively referred to as "TL" hereinafter).

(c) Blood plasma 9 ml of blood was collected from a vein of an ear of the rabbit using a plastic injector (Terumo syringe) into which 1 ml of a 3.13% sodium citrate solution was placed in advance. The blood was mixed and was immediately centrifuged at 3000 r.p.m. for 10 minutes to separate the blood plasma, which was then stored in a cool place at a temperature of 4° to 10° C. and used for the experiment.

(d) Preparation of tissue thromboplastin solution

Commercially available thromboplastin for 20 determinations ("Simplastin", registered trademark; thromboplastin of the brain and lung of the rabbit) was dissolved in 4 ml of distilled water for use in the experiment.

(e) Procedures

Measurement was carried out automatically and objectively by use of a Fibrometer (produced by Baltimore Biological Laboratory) for prothrombin time measurement. Namely, 0.1 ml each of SH, SL, and the various TH and TL were separately placed into cells of the Fibrometer, and 0.1 ml of the blood plasma was added to each sample. Next, the Fibrometer was automatically and simultaneously actuated with the addition of 0.1 ml of the thromboplastin solution to measure the clotting time.

4. Results

The results are shown in Table 1. On the basis of these results, the potency (JP Heparin Unit (μ)) was measured for each sample in accordance with the determination method of the Japanese Pharmacopeia with the results shown below:

| heparin calcium | 200 μ/mg |
|---|---|
| heparin having high antithrombin III affinity as defined in the present specification | 390 μ/mg |
| heparin having low antithrombin III affinity, in accordance with the present invention | 3 μ/mg |

TABLE 1

Prothrombin time extending action

| Sample and Concentration | Prothrombin time (sec) | | | |
|---|---|---|---|---|
| | 1st time | 2nd time | 3rd time | 4th time |
| Control (5% glucose) | 9.4 | 9.6 | 9.7 | 9.8 |
| SH (standard heparin 8.53 μ/ml) | 18.7 | 18.3 | 18.8 | 19.3 |
| SL (standard heparin 6.83 μ/ml) | 17.7 | 17.8 | 17.8 | 17.3 |
| $T_1H$ (standard heparin 0.0505 mg/ml) | 18.7 | 18.3 | 20.1 | 19.3 |
| $T_1L$ (standard heparin 0.0401 mg/ml) | 18.3 | 18.1 | 19.2 | 18.7 |
| $T_2H$ (standard heparin 0.0165 mg/ml) | 17.8 | 17.7 | 17.0 | — |
| $T_2L$ (standard heparin 0.0132 mg/ml) | 17.1 | 15.7 | 15.8 | — |
| $T_3H$ (standard heparin 0.475 mg/ml) | 13.3 | 13.2 | 12.9 | — |
| $T_3L$ (standard heparin 0.380 mg/ml) | 12.8 | 12.7 | 12.3 | — |

As described above, the heparin potency measured in accordance with the method stipulated by the Japanese Pharmacopeia represents the potency primarily in terms of the inhibiting activity against exogenous coagulation. Judging from the potency calculated in this Experimental Example, therefore, it can be understood that heparin having low antithrombin III affinity, in accordance with the present invention, (see the values for $T_3H$ and $T_3L$), has hardly any inhibiting activity against exogenous coagulation.

EXPERIMENTAL EXAMPLE 2

Each of the sample solutions used in Experimental Example 1 was diluted with 5% glucose solution to prepare solutions of the graded concentrations of 0.8 μ/ml, 0.4 μ/ml, 0.2 μ/ml, 0.1 μ/ml and 0.05 μ/ml. 0.1 ml each of these solutions was placed into an injector and was mixed with 1.9 ml of the blood collected from the vein of an ear of the rabbit. The whole blood clotting time was measured in accordance with the Lee-White method with the results shown in Table 2.

TABLE 2

Extending action of whole blood clotting time of rabbit blood (average of three runs)

| | Added heparin concentration (μ/ml) | | | | |
|---|---|---|---|---|---|
| Sample | 0.0025 min. | 0.005 min. | 0.01 min. | 0.02 min. | 0.04 min. |
| L | 17 | 39 | 66 | 72 | 89 |
| H | — | — | 13 | 27 | 33 |
| Hc | — | — | 17 | 30 | 39 |
| Control | 10~13 min. | | | | |

In the column of samples above, L, H and Hc represent heparin having low antithrombin III affinity in accordance with the present invention, heparin having high antithrombin III affinity as defined in the present specification and heparin calcium, respectively, and the control represents 5% glucose.

It can be seen from Table 2 that the normal whole blood clotting time of rabbit blood falls within the range of 10 to 13 minutes and the maximum time is 13 minutes. Accordingly, when the heparin concentration required for doubling the whole blood clotting time, as the effect of the heparin dose, that is, up to about 26 minutes at most, was determined by interpolation, it was found to be 0.0035 μ/ml for heparin having low antithrombin III affinity, in accordance with the present invention, 0.0190 μ/ml for heparin having high antithrombin III affinity as defined in the present specification and 0.0160 μ/ml for heparin calcium.

Since the whole blood clotting time in this Experimental Example was measured without applying any exogenous coagulating factors, extension of the clotting time was brought about by the inhibiting activity of heparin against endogenous coagulation.

Accordingly, if the potency is compared in terms of the concentration required for doubling the normal whole blood clotting time, the potency of heparin having low antithrombin III affinity, in accordance with the present invention, is 5.4 times that of heparin having high antithrombin III affinity and 4.6 times that of heparin calcium. In any event, the heparin having low antithrombin III affinity was found to have a potency about five times higher than that of the other two, against endogenous coagulation.

EXPERIMENTAL EXAMPLE 3

1. Sample and dose

The samples used were heparin having low antithrombin III affinity (3 $\mu$/mg, JP Heparin Units) in accordance with the present invention, heparin having high antithrombin III affinity (390 $\mu$/mg, JP Heparin Units), as defined in the present specification and heparin calcium (200 $\mu$/mg, JP Heparin Units). Since it was clarified from the results of Experimental Example 2 that heparin having low antithrombin III affinity, in accordance with the present invention, had an inhibiting activity against endogenous coagulation about five times greater than that of the other two, the dose of heparin having low antithrombin III affinity employed was 1/5 in unit,: calculated as JP Heparin Units, of the doses of the other two, or, 20$\mu$ (JP Heparin Units)/kg.

2. Animals

White male native rabbits weighing from 2.8 to 3.6 kg were kept for at least one month in a chamber at 21° to 25° C. and were fed 100 g/day of a solid feed for rabbits, ORC-4 (produced by Oriental Kobo K.K.) and were permitted to take service water freely.

3. Dose of drug and blood collecting condition

A predetermined dose was administered to the vein of the left ear of the rabbit and 2 ml samples of the blood were collected from the vein of the right ear after 15, 30, 60 and 120 minutes after the administration. The blood was also collected immediately before administration as a control. The blood collecting time was within 2 minutes in all cases.

4. Coagulation activity measuring method

The whole blood clotting time was measured by the Lee-White method. Namely, 2 ml of the blood was collected from the vein of the ear using a 2.5 ml plastic injector (Jintan Terumo K.K.). A stop watch was immediately started and 1 ml of the collected blood was quickly placed into each of two test tubes (8 mm inner diameter, 10 cm long), which were placed in hot water at 37° C. After five minutes from the blood collection, one of the test tubes was inclined every minute and from the time at which the contents of that test tube no longer exhibited fluidity, the other tube was also inclined in the same way to observe blood coagulation. The period from the blood collection until the finish of the blood coagulation of the second test tube was taken as the whole blood clotting time.

The normal value of the whole blood clotting time of the rabbit was from 6.5 to 12.5 minutes, using as such a range the time in which 99% of the measured values of the twelve normal rabbits fell (average value $\pm 3\sigma$).

5. Results

The results are shown in FIG. 1.

It can be seen from FIG. 1 that heparin having low antithrombin III affinity, in accordance with the present invention, heparin having high antithrombin III affinity as defined in the present specification and heparin calcium exhibited the same behavior in the duration of their inhibiting activity against endogenous coagulation when the doses were made at the same level of the inhibiting activity against endogeneous coagulation.

EXPERIMENTAL EXAMPLE 4

1. Samples

The samples used were heparin having low antithrombin III affinity, in accordance with the present invention (3 $\mu$/mg, JP Heparin Units), heparin having high antithrombin III affinity as defined in the present specification (390 $\mu$/mg, JP Heparin Units) and heparin calcium (200 $\mu$/mg, JP Heparin Units).

2. Animals

SD type male rats (S.P.F.) weighing from 230 to 280 g.

3. Method of experiment

Heparin having low antithrombin III affinity, in accordance with the present invention, heparin having high antithrombin III affinity as defined in the present specification and heparin calcium were intravenously administered to the vein of the rat tail in the doses of 20 $\mu$/kg and 100 $\mu$/kg, 100 $\mu$/kg and 500 $\mu$/kg, and 100 $\mu$/kg and 500 $\mu$/kg, respectively. The dosing solution quantity and the dosing rate were 0.1 ml/100 g and about 10 sec/0.1 ml, respectively. A 5% glucose injection solution was administered as a control.

The bleeding time was measured in accordance with the method of Cliffton et al. Namely, the rats were placed in a plastic fixation box and each heparin was administered to non-anesthesized rats. After 15 minutes from the heparin administration, the right vein 7 cm distant from the tail tip was cut with a knife and filter paper was put on the cut portion to measure the bleeding time by observing whether or not the blood penetrated the filter paper. When the bleeding was vigorous, the filter paper was placed on the cut portion about every five minutes and when the bleeding seemed to be about to stop, the filter paper was placed on the cut portion every minute.

4. Results

Table 3 illustrates the results of measurements of the bleeding time 15 minutes after the heparin administration. For reference, the results of Experimental Example 3 for the measurement of the whole blood clotting time after 15 minutes after the heparin administration to the rabbits are also shown in Table 3.

TABLE 3

| | Bleeding time and the whole blood clotting time | | | |
|---|---|---|---|---|
| Sample | Dose $\mu$/kg (mg/kg) | No. of cases | Bleeding time (min) | Whole blood clotting time (min) |
| control | — | 9 | 47 ± 15 | (normal 9 ± 1) |
| Hc | 100 (0.5) | 8 | 75 ± 16 | 29 ± 8 |
| | 500 (2.5) | 6 | 168 ± 19 | — |
| H | 100 (0.25) | 6 | 73 ± 19 | 26 ± 8 |
| | 500 (1.25) | 6 | 191 ± 19 | — |
| L | 20 (6.7) | 6 | 49 ± 19 | 28 ± 8 |
| | 100 (33.3) | 6 | 67 ± 19 | — |

In the column entitled "Sample", control represents 5% glucose and symbols Hc, H and L represent heparin calcium, heparin having high antithrombin III affinity as defined in the present specification and heparin having low antithrombin III affinity, in accordance with the present invention, respectively. Both bleeding time (minute) and whole blood clotting time are expressed in terms of the mean value ±95% confidence limits in each number of subjects.

The following facts can be found from Table 3.

When the bleeding time of the three types of heparin materials is compared in terms of the dose required for providing a whole blood clotting time of about 26 to about 29 minutes as an average value, for example, the bleeding time is 75 minutes and 73 minutes on the average for heparin calcium and heparin having high antithrombin III affinity as defined in the present specification, whereas it is 49 minutes for heparin having low antithrombin III affinity, in accordance with the present invention. The average value of the bleeding time is 47 minutes in the 5% glucose dose (control). Hence, prolongation of the bleeding time is not observed in practice when heparin having low antithrombin III affinity, in accordance with the present invention, is administered in the above-mentioned dose.

In the inhibiting activity against endogenous coagulation, the dose of 500μ (JP Heparin Units)/kg of heparin calcium, 500μ (JP Heparin Units)/kg of heparin having high antithrombin III affinity as defined in the present specification and 100μ (JP Heparin Units)/kg of heparin having low antithrombin III affinity, in accordance with the present invention, are substantially equal to one another, judging from the results of Experimental Example 2. When the bleeding time of the three is compared at this level of dose, the bleeding time is 168, 191 and 67 minutes, on the average, respectively. It is thus found that heparin having low antithrombin III affinity, in accordance with the present invention, has a far smaller danger of causing bleeding than the other two heparin materials.

Acute toxicity test

The samples used were heparin having low antithrombin III affinity, in accordance with the present invention (3 μ/mg, JP Heparin Units), heparin having high antithrombin III affinity as defined in the present specification (390 μ/mg, JP Heparin Units) and heparin calcium (200 μ/mg, JP Heparin Units).

500 mg/kg to 1000 mg/kg of each heparin material was intravenously administered to ddY type male mice weighing from 23 to 27 g and the acute toxicity was examined in the course of 10 days. Tonic spasm appeared on the posterior feet in 3/10 of the cases of the group that received a dose of 1000 mg/kg of heparin having high antithrombin III affinity and in 2/10 of the cases of the group that received a dose of 1000 mg/kg dose of heparin calcium, at 20 to 120 seconds after the administration and death due to respiratory paralysis was observed. However, the other groups survived for 10 days after the administration.

Accordingly, it was found that $LD_{50}$ of heparin having low antithrombin III affinity, in accordance with the present invention, in the intravenous administration was at least 1000 mg/kg.

Incidentally, the mice had been raised in a chamber maintained at a temperature of 21°–25° C., wherein each group of 10 mice were placed in a cage and were fed a solid feed CE-2 (produced by Nippon Clair K.K.) and were permitted to freely take water from a water bottle.

The following Working Examples will further clarify the present invention.

WORKING EXAMPLE 1

Cephalose CL-4B was activated by cyanogen bromide in a conventional manner and 200 mg of purified cow antithrombin III, dissolved in 200 ml of 0.2 M-NaHCO$_3$ solution (pH 9.0), was suspended therein. The suspension was gently stirred at 4° C. for 24 hours and was then filtered. It was washed three times with a 0.2 M-NaHCO$_3$ solution (pH 9.0) and was finally suspended in a 0.2 M-NaHCO$_3$ solution (pH 9.0) to obtain lattice-bound antithrombin III gel.

The lattice-bound antithrombin III gel was packed into a column of 2.5 cm diameter and 26 cm length and was buffered by the addition thereto of a 0.05 M-tris-hydrochloric acid buffer (pH 7.5, NaCl 0.15 M). Separately, 10 mg of heparin calcium was dissolved in 2 ml of a 0.05 M-tris-hydrochloric acid buffer (pH 7.5, NaCl 0.15 M) and was applied to the column. 300 ml of a 0.05 M-tris-hydrochloric acid buffer (pH 7.5, NaCl 0.15 M) was passed through the column at a rate of 30 ml/hour, and 10 ml fractions were collected. The fractionation was effected while detecting heparin in each fraction by the carbazole method until outflow of unadsorbed heparin was no longer confirmed.

The fractions containing unadsorbed heparin were collected, desalted, concentrated (by ultrafiltration using a Diaflow UM-2) and were again permitted to flow out through the lattice-bound antithrombin III. Ethanol was added to the effluent to form precipitates, which were filtered, again dissolved and freeze-dried, thereby obtaining 5.4 mg of heparin having low antithrombin III affinity, in accordance with the present invention. 300 ml of a 0.05-tris-hydrochloric acid buffer (pH 7.5, NaCl 1.0 M) was further passed through the column, from which no outflow of unadsorbed heparin was confirmed any longer, at a rate of 30 ml/hour and was then desalted and concentrated (by ultrafiltration using a Diaflow UM-2). Ethanol was then added to form precipitates, which were collected by filtration, dissolved again and freezedried, thereby proving 4.2 mg of heparin having high antithrombin III affinity.

The procedures of the above-mentioned column chromatography were repeated six times to obtain 30 mg in total of heparin having low antithrombin III affinity and 22 mg in total of heparin having high antithrombin III affinity.

25 mg of heparin having low antithrombin III affinity obtained in the above-mentioned manner was dissolved in a physiological salt solution to obtain a 50 ml solution and was subjected to the sterile filtration and was packed into an ampule.

WORKING EXAMPLE 2

500 mg of heparin having low antithrombin III affinity was produced in the same way as in Working Example 1 except that the production scale was expanded.

500 mg of heparin thus obtained was dissolved in a physiological salt solution to form a 50 ml solution, was subjected to the sterile filtration and was packed into a vial.

We claim:

1. A method of treating a mammal to inhibit endogenous coagulation of the circulating blood which comprises administering to said mammal, by intravenous administration or intramuscular injection, a therapeutically effective amount of an anticoagulant composition consisting essentially of heparin having low antithrombin III affinity as an effective ingredient, in combination with a pharmacologically acceptable carrier, diluent or vehicle.

2. A method as claimed in claim 1 wherein said heparin having low antithrombin III affinity is a heparin which is not adsorbed by lattice-bound antithrombin III at a physiological pH and in a physiological salt concentration.

3. A method as claimed in claim 2 wherein said physiological pH is in the range of pH 7 to pH 8.

4. A method as claimed in claim 2 or claim 3 wherein said physiological salt concentration is in the range of 0.05 M to 0.20 M, calculated as sodium chloride concentration.

5. A method as claimed in claim 2 or claim 3 wherein said lattice is cephalose CL-4B.

6. A method as defined in claim 4 wherein said lattice is cephalose CL-4B.

7. A method as claimed in claim 1, wherein said anticoagulant composition is in the form of an injectable liquid composition consisting of a therapeutically effective amount of said heparin having low antithrombin III affinity and water or isotonic saline.

8. A method of treating a human being to inhibit the endogenous coagulation of the circulating blood which comprises administering to said human being, by intravenous administration or intramuscular injection, a therapeutically effective amount of a liquid anticoagulant composition consisting of a therapeutically effective amount of heparin having low antithrombin III affinity, and water or isotonic saline.

* * * * *